United States Patent
De Leon et al.

(10) Patent No.: US 10,122,978 B2
(45) Date of Patent: Nov. 6, 2018

(54) HARMONIZING A PROJECTED USER INTERFACE

(71) Applicant: Sony Corporation, Tokyo (JP)

(72) Inventors: David De Leon, Lund (SE); Ola Thorn, Lund (SE); Magnus Midholt, Lund (SE)

(73) Assignees: SONY CORPORATION, Tokyo (JP); SONY MOBILE COMMUNICATIONS INC., Tokyo (JP)

( * ) Notice: Subject to any disclaimer, the term of this patent is extended or adjusted under 35 U.S.C. 154(b) by 269 days.

(21) Appl. No.: 14/428,092

(22) PCT Filed: Apr. 1, 2014

(86) PCT No.: PCT/IB2014/060353
§ 371 (c)(1),
(2) Date: Mar. 13, 2015

(87) PCT Pub. No.: WO2015/150868
PCT Pub. Date: Oct. 8, 2015

(65) Prior Publication Data
US 2016/0261835 A1    Sep. 8, 2016

(51) Int. Cl.
*G06F 3/0481* (2013.01)
*H04N 9/31* (2006.01)
(Continued)

(52) U.S. Cl.
CPC ........... *H04N 9/3182* (2013.01); *G03B 17/54* (2013.01); *G06F 1/1673* (2013.01); *G06F 3/014* (2013.01); *G06F 3/017* (2013.01); *G06F 3/0346* (2013.01); *G06F 3/048* (2013.01); *G06F 3/0426* (2013.01); *G06F 3/0481* (2013.01); *G06F 3/0485* (2013.01); *G06F 3/14* (2013.01);
(Continued)

(58) Field of Classification Search
CPC .... H04N 9/3182; G03B 17/54; G06F 1/1673; G06F 3/014; G06F 3/017; G06F 3/0346; G06F 3/0426; G06F 3/048; G06F 3/0481; G06F 3/0485; G06F 3/14; G06F 3/04886
See application file for complete search history.

(56) References Cited

U.S. PATENT DOCUMENTS 6,771,294 B1 *   8/2004   Pulli ................... G06F 3/011
                                                345/173
8,228,315 B1 *   7/2012   Starner ............... G02B 27/017
                                                345/175

(Continued)

OTHER PUBLICATIONS

International Search Report and Written Opinion dated Feb. 11, 2015 for corresponding application No. PCT/IB2014/060353 filed Apr. 1, 2014.

*Primary Examiner* — Amare Mengistu
*Assistant Examiner* — Crystal A Mathews
(74) *Attorney, Agent, or Firm* — Renner Otto Boisselle and Sklar

(57) ABSTRACT

The present disclosure provides a projection device for adapting a property of a projected user interface. The device determines at least one property of a surface onto which a user interface is projected. The property of the projected user interface is changed based on the at least one property of the surface onto which the projected user interface is projected.

24 Claims, 6 Drawing Sheets

(51) Int. Cl.
  *G06F 1/16* (2006.01)
  *G06F 3/01* (2006.01)
  *G06F 3/042* (2006.01)
  *G06F 3/048* (2013.01)
  *G06F 3/0346* (2013.01)
  *G03B 17/54* (2006.01)
  *G06F 3/0485* (2013.01)
  *G06F 3/14* (2006.01)
  *G06T 13/80* (2011.01)

(52) U.S. Cl.
  CPC ............ *G06T 13/80* (2013.01); *H04N 9/3185* (2013.01); *H04N 9/3194* (2013.01); *G01N 2291/02827* (2013.01); *G06T 2200/24* (2013.01)

(56) References Cited

U.S. PATENT DOCUMENTS

| | | | |
|---|---|---|---|
| 8,982,104 B1* | 3/2015 | Fujishima | G06F 3/023 178/18.04 |
| 9,007,321 B2* | 4/2015 | Adachi | G06F 3/013 345/173 |
| 9,367,142 B2* | 6/2016 | Lee | G06F 3/0304 |
| 9,489,128 B1* | 11/2016 | Zhang | G06F 3/04886 |
| 2004/0207652 A1* | 10/2004 | Ratti | G06F 3/0425 345/697 |
| 2008/0013057 A1* | 1/2008 | Bullock | G09G 3/002 353/121 |
| 2008/0043205 A1 | 2/2008 | Lonn | |
| 2008/0044005 A1* | 2/2008 | Johnston | H04M 1/0272 379/433.01 |
| 2008/0303799 A1* | 12/2008 | Schwesig | G06F 3/0414 345/173 |
| 2009/0168027 A1* | 7/2009 | Dunn | G03B 21/26 353/28 |
| 2009/0190046 A1 | 7/2009 | Kreiner et al. | |
| 2010/0004772 A1* | 1/2010 | Elfstrom | G06Q 10/06 700/103 |
| 2010/0199232 A1* | 8/2010 | Mistry | G06F 1/163 715/863 |
| 2011/0133934 A1* | 6/2011 | Tan | G06F 1/163 340/573.1 |
| 2012/0008871 A1 | 1/2012 | Kim | |
| 2012/0050689 A1 | 3/2012 | Cudak et al. | |
| 2012/0139689 A1* | 6/2012 | Nakade | G08C 17/02 340/4.3 |
| 2012/0249409 A1* | 10/2012 | Toney | G06F 3/017 345/156 |
| 2012/0293402 A1* | 11/2012 | Harrison | G06F 3/017 345/156 |
| 2013/0016070 A1* | 1/2013 | Starner | G02B 27/017 345/175 |
| 2013/0086531 A1* | 4/2013 | Sugita | G06F 3/017 715/863 |
| 2013/0229396 A1* | 9/2013 | Huebner | H04N 9/3147 345/207 |
| 2013/0257640 A1* | 10/2013 | de Wilde | G01S 7/022 342/20 |
| 2013/0314550 A1* | 11/2013 | Litvinov | H04N 1/603 348/177 |
| 2013/0322785 A1* | 12/2013 | Kamamori | G06F 3/0484 382/311 |
| 2014/0016099 A1* | 1/2014 | Choi | E04H 3/22 353/30 |
| 2014/0055352 A1* | 2/2014 | Davis | G06F 3/017 345/156 |
| 2014/0111415 A1* | 4/2014 | Gargi | G06F 3/017 345/156 |
| 2014/0177909 A1* | 6/2014 | Lin | G06F 19/00 382/103 |
| 2014/0333585 A1* | 11/2014 | Suzuki | G06F 3/0425 345/175 |
| 2015/0109261 A1* | 4/2015 | Masuda | H04N 9/3129 345/175 |
| 2015/0189248 A1* | 7/2015 | Shin | H04N 9/3182 348/745 |
| 2015/0222842 A1* | 8/2015 | Kwong | H04N 9/3182 348/745 |
| 2015/0268730 A1* | 9/2015 | Walline | G06F 3/017 345/168 |
| 2015/0332075 A1* | 11/2015 | Burch | G06K 7/10821 345/156 |
| 2016/0036900 A1* | 2/2016 | Gallagher | G11B 27/034 709/204 |
| 2016/0188181 A1* | 6/2016 | Smith | G06F 3/048 715/765 |

* cited by examiner

HARMONIZING A PROJECTED USER INTERFACE

This application is a national phase of International Application No. PCT/IB2014/060353 filed Apr. 1, 2014 which is hereby incorporated herein by reference

TECHNICAL FIELD

The present invention relates to a system for projecting a user interface and more particularly to a method and system for harmonizing a projected user interface with the physical properties of the surface onto which the user interface is projected.

BACKGROUND OF THE INVENTION

Personal computing devices are beginning to incorporate user interfaces that are projected onto an external surface. Current systems allow a user to interact with the projected user interface by moving their fingers over the projected user interface to select keys and entered commands via the user interface.

SUMMARY OF THE INVENTION

Current projected user interfaces are limited in that the projected user interfaces are not adjusted based on the properties of the surface onto which the user interface is projected. That is, the same user interface is projected in the same way regardless of, e.g., the color/patterning of the surface, the softness or hardness of the surface, etc.

This disclosure describes a method for adapting a property of a projected user interface based on at least one property of a surface on to which the projected user interface is projected.

According to one aspect of the disclosure, there is provided a method for adapting a property of a projected user interface based on at least one property of a surface on to which the projected user interface is projected. The method includes determining the at least one property of the surface, determining a relevant user interface setting based on the determined at least one property of the surface, and applying the determined relevant user interface setting to the projected user interface, such that the property of the projected user interface is changed according to the determined user interface setting.

Alternatively or additionally, the property of the projected user interface that is changed affects updating of the projected user interface due to user interaction with the projected user interface.

Alternatively or additionally, the at least one property of the surface is at least one of the coloring of the surface, the texture of the surface, the deformability of the surface, the orientation of the surface, the hardness of the surface, or the topography of the surface.

Alternatively or additionally, the at least one property of the surface is measured during user interaction with the projected user interface.

Alternatively or additionally, the projected user interface is updated such that at least one of animations or sound effects of the projected user interface appear to match the at least one property of the surface.

Alternatively or additionally, the determined relevant user interface setting is applied such that the projected user interface appears substantially homogeneous across color variations of the surface or such that the contrast between the projected user interface and the surface is approximately constant across the surface despite color variations of the surface.

Alternatively or additionally, the at least one property of the surface is determined using a camera.

Alternatively or additionally, the camera measures at least one of visual distortion of the projected user interface during user input to determine deformability of the surface or coloring of the surface.

Alternatively or additionally, the camera measures visual distortion of the projected user interface during user input by analyzing deformation of the projected user interface during user interaction with the projected user interface.

Alternatively or additionally, the at least one property of the surface is determined using an acoustic sensor and the at least one property of the surface is determined based on the sound generated by the user interacting with the surface.

Alternatively or additionally, the at least one property of the surface measured using the acoustic sensor is at least one of a type of material of the surface or a hardness of the surface.

Alternatively or additionally, the at least one property of the surface is determined using a user worn device.

Alternatively or additionally, the user worn device includes at least one of an accelerometer or a gyroscope configured to capture measurements of user movements during interaction with the projected user interface.

Alternatively or additionally, a processor analyzes the captured measurements to determine at least one of the hardness of the surface or the deformability of the surface.

Alternatively or additionally, the at least one property of the surface is determined based on geo-location coordinates of the projected user interface.

Alternatively or additionally, the geo-location coordinates of the projected user interface are determined using at least one of near field communication, Bluetooth, Geo fencing, indoor Wi-Fi positioning, or GPS.

Alternatively or additionally, the user manually selects the relevant user interface setting for the surface and a current location of the user is tagged such that the selected relevant user interface setting are automatically selected to be the relevant user interface setting for user interfaces projected at the current location.

Alternatively or additionally, if the surface is determined to be deformable, the projected user interface is updated to increase the size of elements of the projected user interface.

Alternatively or additionally, on a less deformable surface, a pressed button results in a hard surface animation. On a more deformable surface, a pressed button results in a soft surface animation.

Alternatively or additionally, at least one of: the hard surface animation results in an element of the user interface bouncing higher than the soft surface animation or the hard surface animation is a hard scrolling animation that behaves differently than a soft scrolling animation by at least one of responding quicker, scrolling faster, or scrolling for a longer time.

According to another aspect of the disclosure, there is provided a projecting device for projecting a user interface onto a surface and for adapting a property of the projected user interface based on at least one property of the surface. The device includes a projector, a sensor, and a processor. The projector is configured to project the user interface onto the surface. The sensor is configured to determine the at least one property of the surface. The processor is configured to determine a relevant user interface setting based on the determined at least one property of the surface and control the user interface projected by the projector such that the property of the projected user interface is changed according to the determined user interface setting.

According to a further aspect of the disclosure, there is provided a system for projecting a user interface onto a surface and for adapting a property of the projected user interface based on at least one property of the surface. The system includes the projecting device and a computing device in communication with the projecting device.

Alternatively or additionally, the computing device includes the projecting device.

A number of features are described herein with respect to embodiments of this disclosure. Features described with respect to a given embodiment also may be employed in connection with other embodiments.

For a better understanding of the present disclosure, together with other and further aspects thereof, reference is made to the following description, taken in conjunction with the accompanying drawings. The scope of the disclosure is set forth in the appended claims, which set forth in detail certain illustrative embodiments. These embodiments are indicative, however, of but a few of the various ways in which the principles of the disclosure may be employed.

DETAILED DESCRIPTION OF THE INVENTION

Figure 1:
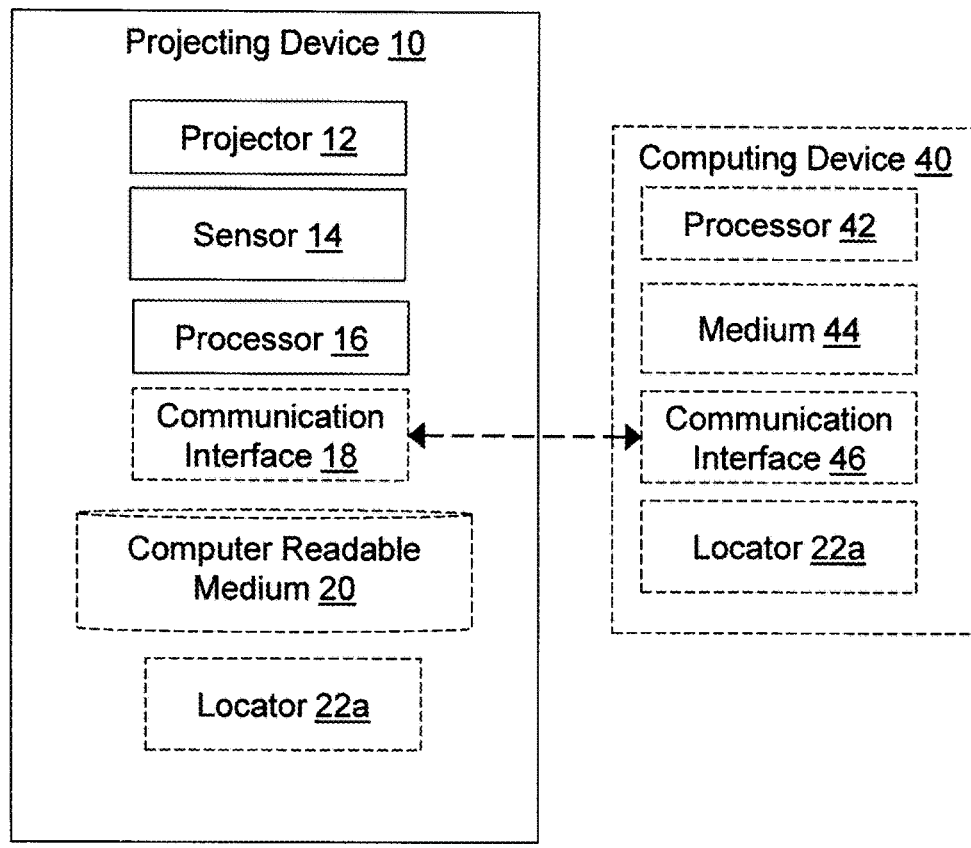
FIG. 1 is a block diagram representing the architecture of a projecting system including a projecting device.

The present invention is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

It should be appreciated that many of the elements discussed in this specification may be implemented in a hardware circuit(s), a processor executing software code or instructions which are encoded within computer readable media accessible to the processor, or a combination of a hardware circuit(s) and a processor or control block of an integrated circuit executing machine readable code encoded within a computer readable media. As such, the term circuit, module, server, application, or other equivalent description of an element as used throughout this specification is, unless otherwise indicated, intended to encompass a hardware circuit (whether discrete elements or an integrated circuit block), a processor or control block executing code encoded in a computer readable media, or a combination of a hardware circuit(s) and a processor and/or control block executing such code.

The present disclosure provides a projection device for adapting a property of a projected user interface. The device determines at least one property of a surface onto which a user interface is projected. The property of the projected user interface is changed based on the at least one property of the surface onto which the projected user interface is projected.

By having the projected user interface harmonize with attributes of the underlying surface, it is possible to create a more cohesive experience in which the surface and the projected user interface are experienced as one object. By harmonizing the user interface with the physical properties of the underlying surface, it is possible to transfer those properties to the user interface, resulting in a richer experience for the user.

An exemplary projecting system 8 including a projecting device 10 and computing device 40 is depicted in FIG. 1. The exemplary projecting device 10 may be included as part of a computing device. Alternatively, as shown in FIG. 1, the projecting device 10 may be separate from the computing device 40. The projecting device 10 includes a projector 12, a sensor 14, and a processor 16. The sensor 14 is configured to determine at least one property of the surface onto which the user interface is projected by the projector 12. The processor 16 determines a relevant user interface setting based on the at least one property of the surface determined by the sensor 14. The processor 16 then controls the user interface projected by the projector 12 such that the property of the projected user interface is changed according to the determined user interface setting. For example, the user interface may be projected using an animation that simulates the properties of an element bouncing on the surface. In this example, if the sensor 14 determines that the surface is a hard surface, the user interface may be projected using a hard surface animation. In the hard surface animation, an element of the user interface simulates the behavior of a real world object by bouncing higher than the same element would bounce on a softer surface.

As described above, the projecting device 10 may be included as part of or communicates with a computing device 40. For example, the projecting device 10 may be included as part of or used with a mobile phone, tablet computer, mobile PC, laptop, handheld gaming device, desktop PC, gaming console, or any other suitable electronic device. If the projecting device 10 is a separate device that communicates with the computing device 40, a communication interface 18 on the projecting device 10 and a communication interface 46 on the computing device 40 may be used to establish a wired or wireless operative interface there-between. As would be understood by one of ordinary skill in the art, the communication interface 18, 46 of the projecting device 10 and computing device 40 may comprise a USB interface, a wireless network adaptor, an Ethernet network card, a Bluetooth adaptor, a near field communication (NFC) adaptor, an infrared communication adaptor, a radio frequency communication interface, or any suitable device that provides a communication channel between the projecting device 10 and the computing device 40.

The communication interface 18 of the projecting device 10 may be communicatively coupled to a computer readable medium 20, such that the communication interface 18 is able to send data stored on the computer readable medium 20 to the computing device 40. The communication interface 18 may also be communicatively coupled to the processor 16 such that the processor 16 is able to control operation of the communication interface 18.

The computing device 40 may additionally include a processor 42 and a non-transitory computer readable medium 44. As described above regarding the projecting device 10, the communication interface 46 may be communicatively coupled to the computer readable medium 44 and processor 42.

As described above, the detecting device 10 includes a sensor to determine at least one property of the surface onto which the user interface is projected. The sensor 14 may include a camera, acoustic sensor, ultrasonic sensor, spectrometer, gyroscope, accelerometer, and/or any other device suitable for determining at least one property of the surface. For example, the sensor 14 may be a camera that is used to determine at least one of (1) a visual distortion of the projected user interface during user input to determine deformability of the surface or (2) coloring of the surface. Both these examples are described below in regards to FIGS. 2A and 2B and FIGS. 4A and 4B.

Figure 2A:
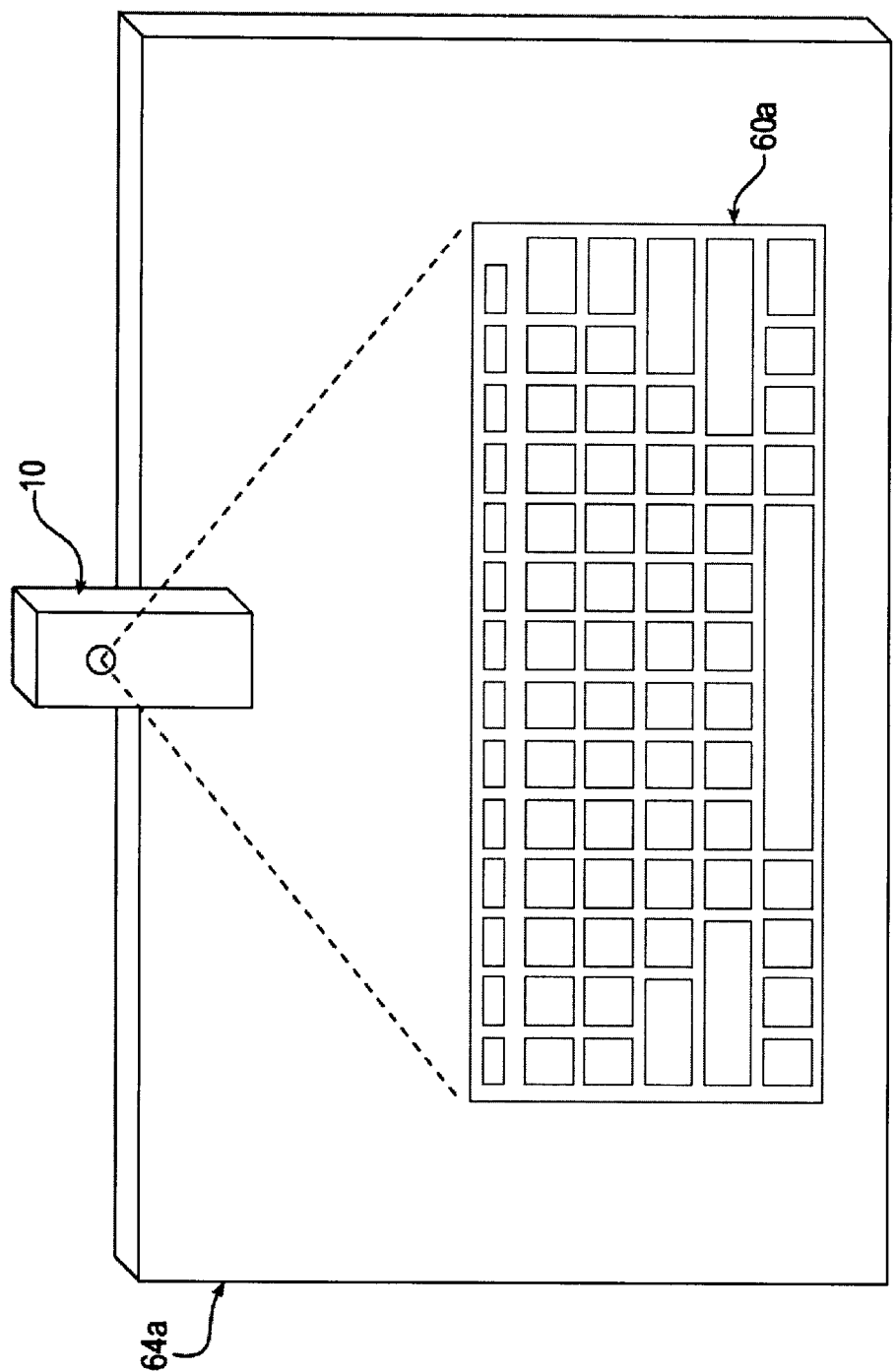
FIG. 2A depicts a user interface projected onto a surface having a uniform appearance.
Figure 2B:
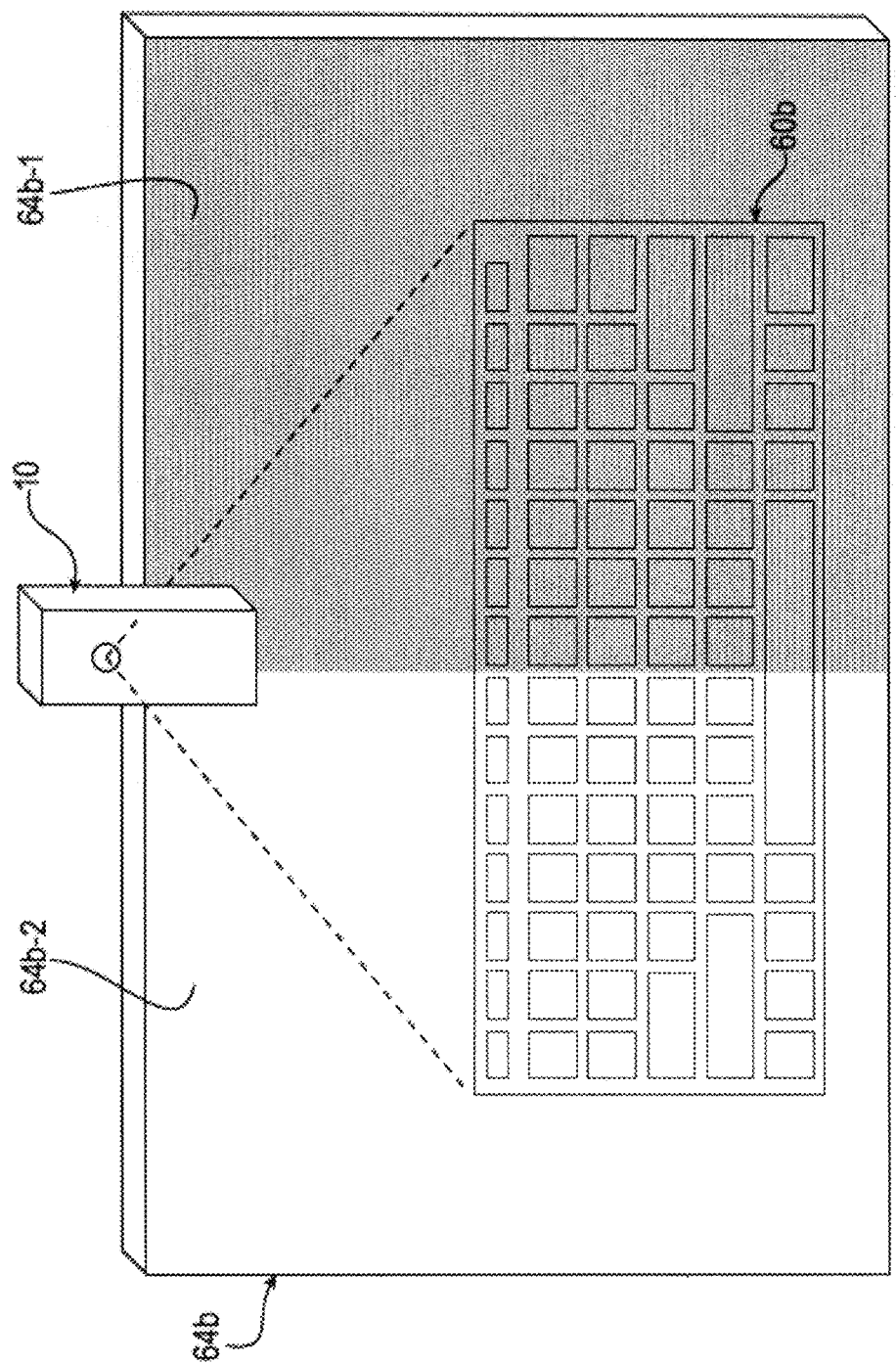
FIG. 2B depicts a user interface projected onto a surface having a non-uniform appearance.

Turning to FIGS. 2A and 2B, an exemplary projected user interface 60 is shown projected onto two different surfaces. In FIG. 2A, the user interface 60*a* has been projected onto a surface 64*a* having an approximately uniform color and texture. In FIG. 2B, the same user interface 60 has been projected onto a surface 64*b* having a non-uniformly colored surface 64. In both examples, the sensor 14 is used to determine the surface coloring. As will be understood by one of ordinary skill in the art, surface coloring may refer to the color of the surface as well as shading, reflectivity, a shadow cast on the surface, or any other optical properties of the surface 64 that affect the appearance of the surface 64.

As shown in FIG. 2B, the projected user interface 60 has been adjusted such that the projected user interface 60 does not vary significantly in contrast across the surface due to variations in optical properties of the surface 64*b*. In this example, the darkness of the projected user interface 60*b* (i.e., a keyboard) has been increased in the darker areas 64*b*-1 compared to the lighter area 64*b*-2 of the surface 64*b* such that the contrast between the projected user interface 60 and the surface 64 is relatively constant across the projected user interface 60. The projected user interface 60 need not be adjusted such that the contrast is constant across the user interface 60, but rather may be adjusted such that the contrast is sufficient to distinguish the projected user interface 60 from the surface 64 across the projected user interface 60. While the projected user interface 60 is adjusted in this example to be made darker depending on the local properties of the surface 64, the projected interface 60 may also be adjusted to be made brighter to achieve sufficient contrast between the surface 64 and the projected user interface 60. Adjustments to the projected user interface 60 may include the color and brightness of the projected user interface 60. The adjustments to the projected user interface 60 are described below in the FIG. 3 flowchart.

The projected user interface 60 may be adjusted such that the contrast between the projected user interface and the surface is approximately constant across the surface despite color variations in the surface. Approximately constant may refer to the contrast between the projected user interface and surface not varying across the surface by more than 5%, 10%, 20%, 25%, or 50%. Approximately constant may also refer to the apparent contrast between the projected user interface and the surface as experienced by a user viewing the user interface projected onto the surface.

As will be understood by one of ordinary skill in the art, the coloring of the surface 64 may refer to the brightness, hue, intensity, and/or color of the surface 64 onto which the user interface 60 is projected. The coloring of the surface 64 may be effected by the properties of the surface 64 as well as ambient light incident on the surface 64 or light emitted by the surface 64.

Figure 3:
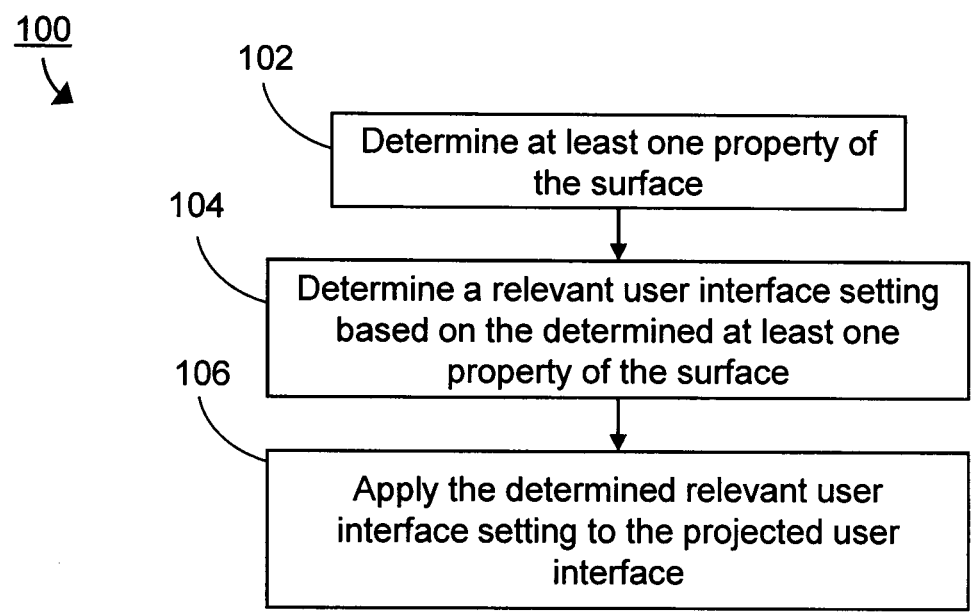
FIG. 3 is a flow diagram representing operation of a method for adapting a property of a projected user interface.

FIG. 3 depicts a method 100 for adapting a property of a projected user interface 60 based on at least one property of a surface 64 on to which the projected user interface 60 is projected. In process block 102, at least one property of the surface 64 onto which the user interface 60 is projected is determined. As described above, this may be determined using the sensor 14 of the projecting device 10. The at least one property of the surface 64 may be at least one of the coloring of the surface 64, the texture of the surface 64, the deformability of the surface 64, the orientation of the surface 64, the slope of the surface 64, the hardness of the surface 64, or the topography of the surface 64. The at least one property of the surface 64 may be measured during user interaction with the projected user interface 60. Alternatively, the at least one property of the surface 64 may be measured when the user is not interacting with the projected user interface 60.

The at least one property of the surface 64 may be constant for a duration of time. For example, the deformability of a surface 64 at a given location may not change with time. Alternatively, the at least one property of the surface 64 at a given location may vary with time. For example, in FIG. 2B the shadowing of the surface 64*b*-1 may be caused by lighting in the vicinity of the surface 64. As will be understood by one of ordinary skill in the art, the light incident on the surface 64 may vary with time. In this case, the at least one property of the surface 64 may be monitored in time such that the steps in the method 100 are repeated at designated intervals or continuously in order to update the projected user interface 60 based on the current conditions affecting light incident on the surface 64.

The at least one property of the surface 64 may also change as the location of the projecting device 10 is changed. For example, if a user picks up the device 10 and moves to a new location (i.e., to a surface 64 having different properties), then the at least one property the surface 64 may need to be determined again. In this example, the projecting device 10 may include a locator 22 or alternative sensor (such as an accelerometer for gyroscope) for detecting when the device 10 is moved. Upon detecting movement, the method 100 may be restarted in order to determine the at least one property of the surface 64 and adjust the user interface settings based on the determined at least one property.

In process block 104, a relevant user interface setting is determined based on the at least one property of the surface 64 determined in process block 102. For example, if the surface 64 is determined to be deformable, the relevant user interface setting may be the size of the user interface elements. The size of the user interface elements may be determined such that the projected user interface 60 is updated to increase the size of elements of the projected user interface 60.

Returning to the example in FIG. 2B, the determined relevant user interface setting may be the color and/or intensity of different areas of the projected user interface 60. In this example, the determined relevant user interface settings may be applied such that the projected user interface 60 appears substantially homogeneous across color variations of the surface 64 or such that the contrast in the projected user interface 60 across the surface 64 is greater than a predetermined threshold.

In one example, a user interface 60 having a red color is projected onto a surface 64 that has a green portion and a blue portion. If the color of the projected user interface 60 was not adjusted, the projected user interface 60 would look different in the green portion of the surface 64 compared to the blue portion of the surface 64. In this example, the color and brightness of the user interface that is projected onto the blue portion of the surface 64 is adjusted compared to the color and brightness of the user interface 60 that is projected onto the green portion of the surface 64 such that the color and brightness of the user interface appears substantially the same in the green portion and the blue portion of the surface 64. Substantially homogenous or substantially the same may refer to the lack of visible color and brightness variations or color and brightness that appears to vary across the projected user interface by less than 5%, 10%, 20%, 25%, 40%, or 50%.

In process block 106, the determined relevant user interface setting from process block 104 is applied to the projected user interface 60, such that the property of the projected user interface 60 is changed according to the determined user interface setting. The projected user interface 60 may be updated such that at least one of animations or sound effects of the projected user interface 60 appear to match the at least one property of the surface 64. For example, the user interface settings and the projected user interface 60 may be updated to match the physics of the underlying surface 64. In one example, a pressed button may result in a hard surface animation on a less deformable surface and a pressed button may result in a soft surface animation on a more deformable surface. The hard surface animation may result in an element of the user interface 60 bouncing higher than a soft surface animation. In another example the hard surface animation may be a hard scrolling animation that behaves differently than a soft scrolling animation by at least one of responding quicker, scrolling faster, or scrolling for a longer time.

In another example, the property of the projected user interface 60 that is changed may affect updating of the projected user interface 60 due to user interaction with the projected user interface 60. For example, a user selecting a key may result in a sound effect (e.g., a key click, a tap sound, etc.) related to the hardness of the surface 64. For a hard surface, the sound effect may be louder and of a shorter duration than a sound effect used for a softer surface. In another example, a user may select a region of the projected user interface 60 in which an animated ball will begin to bounce. The apparent height to which the ball bounces may depend on the hardness of the surface, with the ball bouncing higher for a correspondingly harder surface.

As described above, the relevant user interface settings may also be determined based on the texture of a surface 64 or the topography of the surface 64. In one example, the texture of a surface 64 may be determined based on the visual appearance of the surface 64 (e.g., reflectivity may signify smoothness while small shadows across the surface may signify roughness) and the sounds generated by user interaction with the surface 64. In another example, a surface 64 having a lower coefficient of friction (e.g., a metal or glass surface) may result in faster and more responsive scrolling than a surface 64 having a higher coefficient of friction (e.g., a rubber surface). In a further example, the projected user interface 60 may be altered based on the topography of the surface 64. For example, if the projected user interface 60 is projected onto a curved surface, the projected user interface 60 may be updated such that keys or buttons included in the user interface 60 do not appear stretched or deformed by the curvature of the surface 64. That is, the user interface 60 may be projected such that square or rectangular buttons/keys still appear to be relatively square or rectangular independent of the curvature of the surface 64 that the user interface 60 is projected onto.

As described above, user interface settings may also be applied to the projected user interface 60 to add visual effects that harmonize with the underlying surface 64. As an example, tapping a button on a hard surface may employ a mechanical metaphor (e.g., the button sinking into the surface 64) or leaving a temporary fingerprint. If the same button is instead projected onto a soft surface, tapping on the button might send out ripples across the projected user interface 60. In the same way, acoustic feedback may be updated or added to the projected user interface 60. In one embodiment, triggered sound effects may be from a sound theme designed to match the determined properties of the surface 64 (e.g., hardness). In an alternative embodiment, acoustic feedback (e.g., sounds detected by the projecting device 10) may be generated by the user interacting with the surface 64. The acoustic feedback may then be used to modulate sound associated with the user interface 60. That is, rather than first categorizing the surface 64 as belonging to a particular category and then selecting sound from a prerecorded set, sound generated by the user interacting with the user interface 60 may be analyzed and used to modulate audio sound effects generated by the projecting device 10 in real time.

As another example, the user interface settings may be applied to the projected user interface 60 to add visual effects that harmonize with the slope, orientation, or topography of the surface 64. For example, the surface 64 may be level, sloped, vertical, or level but located above the user (e.g., on the ceiling). The user interface settings may be applied such that a dialog box that is dismissed on a sloped surface slides off of the user interface. The rate at which the dismissed dialog box slides off of the user interface may depend on the slope of the surface, as well as other properties of the surface (e.g., hardness, texture, etc.). In another example, a dismissed dialog box in a user interface projected onto the ceiling may drop towards the user.

In still another example, the user interface 60 may simulate object motion using a physics engine. When a moving object interacts with the surface, the physics engine utilizes the known parameters of the surface to determine how the object will interact with the surface. For example, on a glass surface, the physics engine may assume rigid body motion between a simulated ball and the surface 64. In another example on a deformable surface (e.g., a couch), the physics engine may assume soft body motion or a combination of rigid body motion and soft body motion.

The user interface 60 may also simulate an object of the projected user interface sinking into the surface 64. The manner that the object sinks into the surface may be based on the determined at least one property of the surface. For example, on a rigid surface, the object may slowly sink into the surface in an upright position. On a deformable surface, the same object may rock back and forth before appearing to be pulled under the surface or the object may topple over as it quickly sinks into the surface.

Figure 4A:
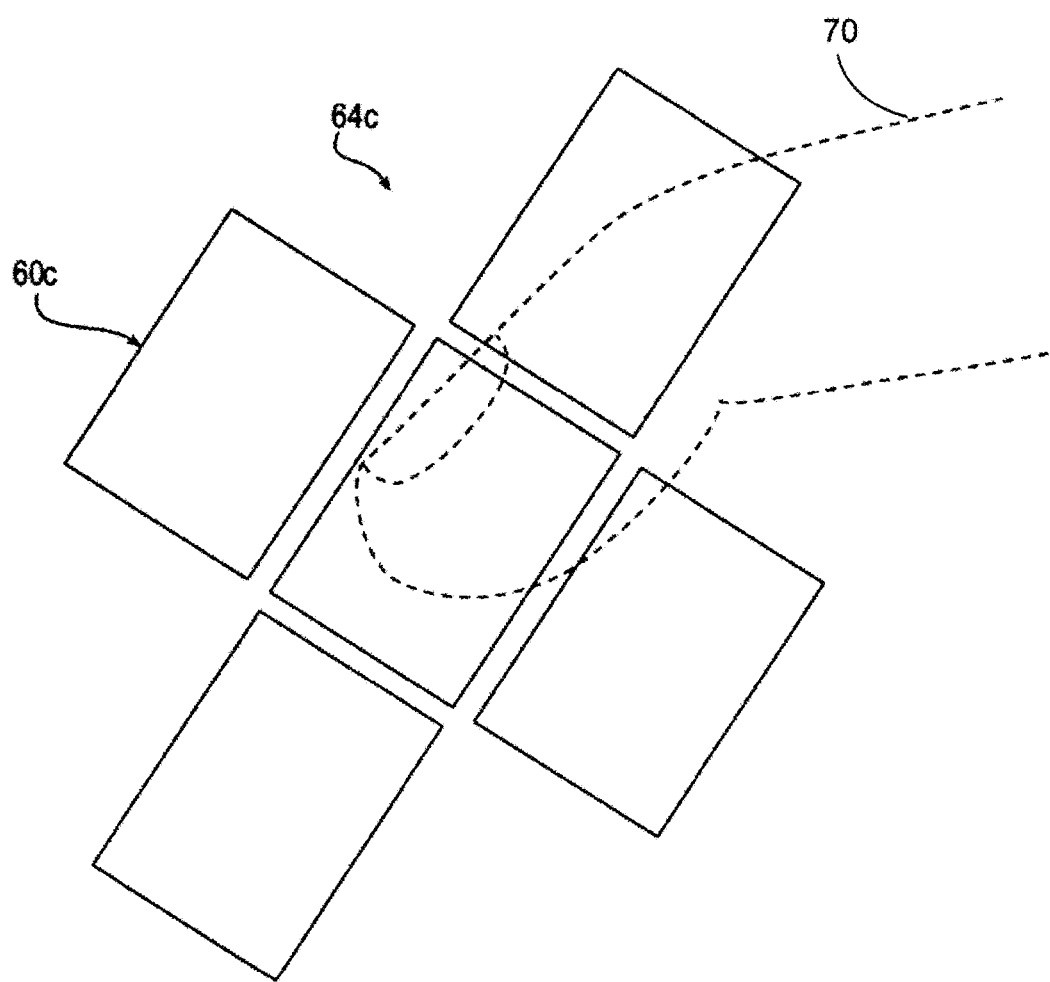
FIG. 4A depicts a user interface projected onto a non-deformable surface.
Figure 4B:
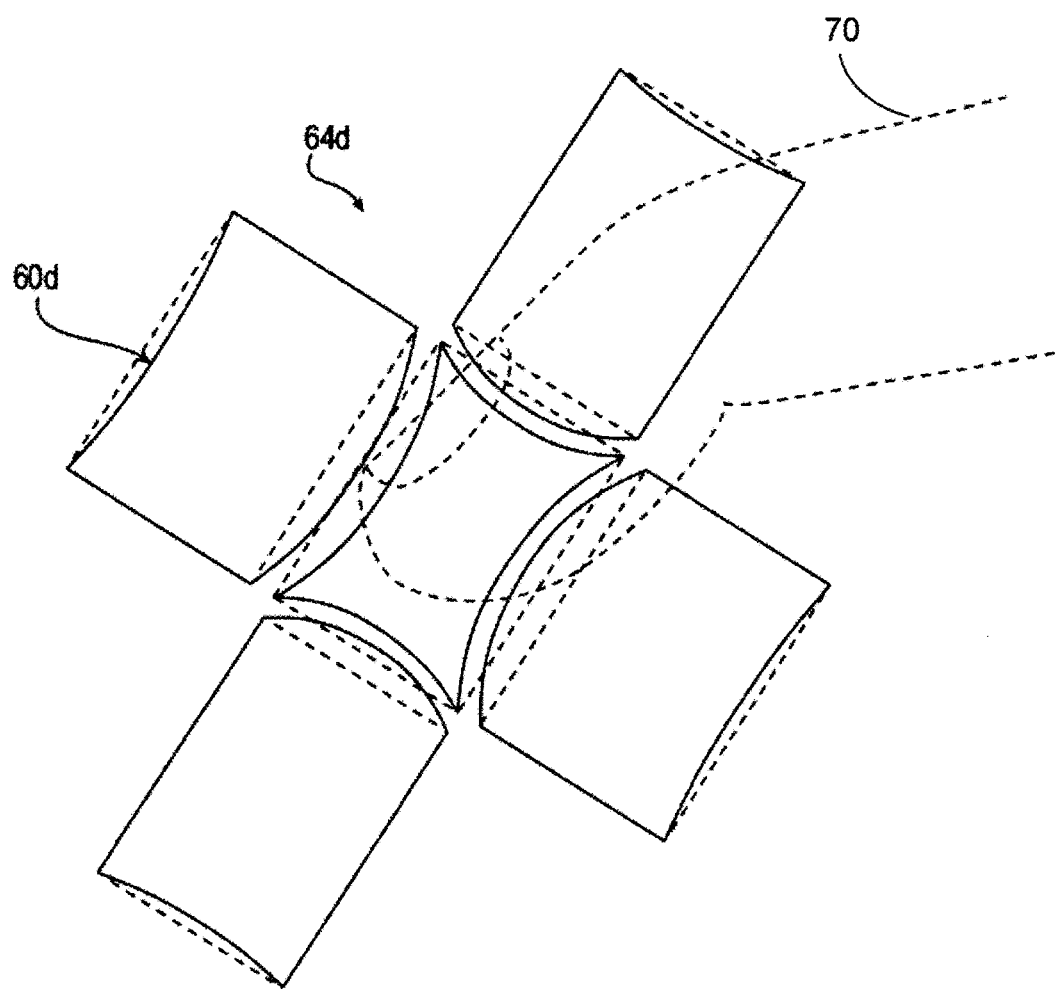
FIG. 4B depicts a user interface projected onto a deformable surface.

Turning to FIGS. 4A and 4B, an exemplary user interface 60 is shown projected onto two different types of surfaces 64. In both figures, a user's finger 70 is shown interacting with the surface onto which the user interface is projected. The user's finger 70 is shown in dashed line in order to better view the projected user interface 60. The user's finger 70 is not shown to interfere with the projected user interface 60 as may be expected in a real world example.

In FIG. 4A, the user interface 60c is projected onto a non-deformable surface 64c. Thus, as shown in the figure, when the user interacts with the projected user interface 60c, the user's finger 70a does not deform the surface 64c.

In FIG. 4B, the user interface 60d is projected onto a deformable surface 64d. When the user interacts with the projected user interface 60d, the user's finger 70b deforms the surface 64 onto which the user interface 60d is projected. The appearance of the projected user interface 60d after deformation of the surface 64d by the user's finger 70b is shown in solid line. The original appearance of the projected user interface 60d before the user's finger 70b deformed the surface 64d is shown in dashed line. As is apparent from the figure, the key that a user presses is deformed along with neighboring keys in the user interface 60d. Portions of the keys that are closer to the point of deformation (i.e., the user's fingertip in the current example) are deformed more strongly than portions of the keys that are farther from the point of deformation. The different amount of deformation across the projected user interface 60d may be used to determine the deformability of the surface 64d as described below.

A camera may be used as the sensor 14 to measure visual distortion of the projected user interface 60 by analyzing deformation of the projected user interface 60 during user interaction with the projected user interface 60. In FIG. 4A, the surface 64c is not deformed by user interaction with the user interface 60c and, thus, the surface 64c is non-deformable. In FIG. 4B, however, the projected user interface 60 is deformed by the user interacting with the projected user interface 60d. Based on the detected deformation of the projected user interface 60d by the sensor 14, the projecting device 10 may determine that the surface 64d is deformable as well as the relative deformability of the surface 64d. For example, the sensor 14 may capture an image of a key that is part of the projected user interface 60 that is deformed during user interaction. The processor 16 may receive the image of the deformed key from the sensor 14 and analyze the image to determine the deformability of the surface 64. The processor 14 may determine the deformability of the surface 64 by first analyzing the image of the deformed key to quantitatively measure the deformation of the key in the image. The processor 14 may measure the deformation of the key by warping an image of the key without deformation until the warped image approximates the image of the deformed key. Based on the parameters of the warp that best approximates the image of the deformed key, the processor 14 may determine the deformability of the surface 64. For example, the computer readable medium 20 may include a table or a function that correlates warp parameters to different properties of the surface 64 (e.g., deformability, hardness, composition, etc.). The processor 14 may use the lookup table to determine one or more properties of a surface 64 that match the warp parameters.

Deformability may not be limited to deformable or non-deformable, but the deformability of a surface may be assigned a qualitative value (e.g., surface deflection in centimeters during user interaction) or may be ranked along a relative scale (e.g., from 1-20). Similar comments apply regarding the other surface properties.

In another example, the user interface 60 may be adapted to counteract distortion of the projected user interface 60 due to deformation of the surface 64 by the user. In this example, the parameters used to modify the projected user interface 60 such that it is not distorted by deformation of the surface 64 may be used to determine the deformability of the surface 64. In this example, the projecting device 10 may perform an iterative process to determine the parameters that correct for the deformation of the user interface 60. Alternatively, the projecting device 10 may project a grid onto the surface 64 using light that is not visible to the human eye (e.g., infrared light). The distortion of the grid by the surface 64 may be used to correct the projected user interface 60 such that distortion of the projected user interface 60 due to deformation of the surface 64 is reduced. The distortion of the grid may also be used to determine properties of the surface 64 (e.g., deformability, hardness, etc.).

As opposed to using a camera to determine the surface type, the sensor 14 may additionally or alternatively include an acoustic sensor. The acoustic sensor may record the sound of the user interacting with the projected user interface 60. The processor 16 may receive the recorded sounds from the sensor 14 and analyze the sounds to determine at least one property of the surface 64. For example, the processor 16 may analyze the recorded sounds to determine a frequency spectrum, amplitude, and duration of the sound. The processor 16 may then compare the determined properties of the recorded sounds to a lookup table stored in the computer readable medium 20 that correlates sound properties to surface properties. For example, the lookup table may correlate a surface composition (e.g., glass, wood, metal, plastic, paper, fabric, padded, etc.) to different frequency spectrum, amplitude, and/or duration of a sound signal. The lookup table may also correlate surface composition to at least one property of the surface 64. For example, the lookup table may correlate glass with a hard, non-deformable, and reflective surface.

As described above, as a user types on the projected keyboard in FIG. 4A, the user's fingers 70 may cause a sound that is different in amplitude, duration, frequency, etc. as compared to the sound detected when the user types on the projected keyboard in FIG. 4B. For example, the sound detected when the user interacts with the projected user interface 60c in FIG. 4A may be louder, have a shorter duration, and/or the frequency spectrum may be higher in frequency than the sound detected when the user interacts with the projected user interface 60d in FIG. 4B. In this way, processor 16 may determine that the surface 64c in FIG. 4A is harder and less deformable than the surface 64d in FIG. 4B.

After determining the at least one property of the surface 64 in FIGS. 4A and 4B, the processor 16 may determine a relevant user interface setting based on the determined at least one property of the surface 64. For example, the processor 16 may use a UI lookup table stored on the computer readable medium 20 that associates surface properties with user interface settings. In one example, the UI lookup table associates non-deformable surfaces with a hard surface animation and hard surface sound effects. Similarly, the UI lookup table may associate deformable surfaces with a soft surface animation and soft surface sound effects.

In another example, the sensor 14 may include a camera that is used by the system 8 to perform object recognition. In this example, the sensor 14 may be used to identify objects which can be assigned properties based on what is known about the identified object. For example, the projecting device 10 may identify that the surface 64 is part of a couch. Based on a model of the couch stored in the system 8, the projecting device 10 may identify properties of the surface 64 (e.g., deformability, texture, etc.) due to the fact that the surface 64 is part of a couch.

The above examples describe using a single surface property to adjust a relevant user interface setting. This should not be interpreted to limit this disclosure to using a single property of the surface to determine relevant user interface settings. Rather, these examples were simply used in order to clarify operation of the projecting device 10. As would be understood by one of ordinary skill in the art, the method 100 and device 10 may use multiple surface properties in order to determine relevant user interface settings. The multiple surface properties may be used individually to determine user interface settings or, alternatively, the multiple surface properties may be used simultaneously to determine the user interface settings. For example, a hard surface may result in one set of user interface settings, while a reflective hard surface may result in a different set of user interface settings.

The above examples describe a user interacting with a projected user interface 60 by touching the surface 64 that the user interface 60 is projected onto. The user may also interact with the user interface 60 by making gestures in the air in front of and/or above the projected user interface.

As will be understood by one of ordinary skill in the art, the processor 16 may have various implementations. For example, the processor 16 may include any suitable device, such as a programmable circuit, integrated circuit, memory and I/O circuits, an application specific integrated circuit, microcontroller, complex programmable logic device, other programmable circuits, or the like. The processor 16 may also include a non-transitory computer readable medium, such as random access memory (RAM), a read-only memory (ROM), an erasable programmable read-only memory (EPROM or Flash memory), or any other suitable medium. Instructions for performing the method described above may be stored in the non-transitory computer readable medium and executed by the processor. The processor 16 may be communicatively coupled to the computer readable medium 20 and communication interface 18 through a system bus, mother board, or using any other suitable structure known in the art.

As will be understood by one of ordinary skill in the art, the computer readable medium 20 may be, for example, one or more of a buffer, a flash memory, a hard drive, a removable media, a volatile memory, a non-volatile memory, a random access memory (RAM), or other suitable device. In a typical arrangement, the computer readable medium 20 may include a non-volatile memory for long term data storage and a volatile memory that functions as system memory for the processor 16. The computer readable medium 20 may exchange data with the processor 16 over a data bus. Accompanying control lines and an address bus between the computer readable medium 20 and the processor 16 also may be present. The computer readable medium 20 is considered a non-transitory computer readable medium.

The at least one property of the surface 64 may also be determined using a user worn device. The user worn device may be a device worn around the wrist, finger, or forearm of the user. The user worn device may include at least one of an accelerometer or a gyroscope configured to capture measurements of user movements during interaction with the projected user interface 60. The processor 16 may analyze the captured measurements to determine at least one of the hardness of the surface 64 or the deformability of the surface 64. For example, when the user interacts with a deformable surface 64 as shown in FIG. 4B, the deceleration experienced by the user worn device due to the user's finger 70 interacting with the surface 64 may be less than when the user interacts with a non-deformable surface 64 as shown in FIG. 4A. Thus, by analyzing the captured measurements, the processor 16 may estimate at least one property of the surface 64.

The user worn device may communicate with the projecting device 10 via the communication interface 18. As described above, the communication interface may communicate with the user worn device via Bluetooth, NFC, infrared, radiofrequency, Wi-Fi, or any other suitable means of wireless or wired communication.

In another embodiment, the at least one property of the surface 64 is determined based on geo-location coordinates of the projected user interface 60. The projecting device 10 may receive the geo-location coordinates via a locator 22 of the projecting device 10 or of the computing device 40. The geo-location coordinates of the projected user interface 60 may be determined using at least one of near field communication, Bluetooth, Geo fencing, indoor Wi-Fi positioning, GPS, or any other suitable technology. The projecting device 10 may determine the at least one property of the surface 64 by searching a database for a stored property of a surface 64 located at the current geo-location. The database may be stored on the computer readable medium 20 of the projecting device 10, on the computing device 40, or in an alternative device such as a server. If the geo-location coordinates are stored in the database, the projecting device 10 may retrieve from the database at least one property of the surface 64 and/or user interface settings associated with the geo-location coordinates. Alternatively, the user may manually select the relevant user interface setting(s) or at least one property for the surface 64 and a current location of the user is tagged such that the selected relevant user interface setting are automatically selected to be the relevant user interface setting for user interfaces 60 projected at the current location. The described database may store user interface setting(s) for a single user or multiple users.

In an alternative embodiment, the user may enter the properties of the surface that the user interface is projected onto. For example, the user could enter the type of surface (e.g., glass, wood, metal, etc.) and/or the surface properties (hardness, deformability, color, etc.).

Although the invention has been shown and described with respect to certain exemplary embodiments, it is obvious that equivalents and modifications will occur to others skilled in the art upon the reading and understanding of the specification. It is envisioned that after reading and understanding the present invention those skilled in the art may envision other processing states, events, and processing steps to further the objectives of system of the present invention. The present invention includes all such equivalents and modifications, and is limited only by the scope of the following claims.

What is claimed is:

1. A method for adapting a property of an interactive projected user interface based on at least one property of a surface on to which the projected user interface is projected, the method comprising:
   determining the at least one property of the surface;
   determining a relevant user interface animation based on the determined at least one property of the surface, wherein the determined relevant user interface animation appears to match a physics of the surface; and
   applying the determined relevant user interface animation based on the determined at least one property of the surface, such that the updating of the projected user interface in response to the user interaction with the elements of the projected user interface is changed according to the determined user interface animation.

2. The method of claim 1, wherein the at least one property of the surface is at least one of the coloring of the surface, the texture of the surface, the deformability of the surface, the orientation of the surface, the hardness of the surface, or the topography of the surface.

3. The method of claim 2, wherein, if the surface is determined to be deformable, the projected user interface is updated to increase the size of elements of the projected user interface.

4. The method of claim 1, wherein the at least one property of the surface is measured during user interaction with the projected user interface.

5. The method of claim 1, wherein the projected user interface is updated such that sound effects of the projected user interface appear to match the at least one property of the surface.

6. The method of claim 1, wherein the determined relevant user interface setting is applied such that the projected user interface appears substantially homogeneous across color variations of the surface or such that the contrast between the projected user interface and the surface is approximately constant across the surface despite color variations of the surface.

7. The method of claim 1, wherein the at least one property of the surface is determined using a camera.

8. The method of claim 7, wherein the camera measures at least one of visual distortion of the projected user interface during user input to determine deformability of the surface or coloring of the surface.

9. The method of claim 8, wherein the camera measures visual distortion of the projected user interface during user input by analyzing deformation of the projected user interface during user interaction with the projected user interface.

10. The method of claim 1, wherein the at least one property of the surface is determined using an acoustic sensor and the at least one property of the surface is determined based on the sound generated by the user interacting with the surface.

11. The method of claim 10, wherein the at least one property of the surface measured using the acoustic sensor is at least one of a type of material of the surface or a hardness of the surface.

12. The method of claim 1, wherein the at least one property of the surface is determined using a user worn device.

13. The method of claim 12, wherein the user worn device includes at least one of an accelerometer or a gyroscope configured to capture measurements of user movements during interaction with the projected user interface.

14. The method of claim 13, wherein a processor analyzes the captured measurements to determine at least one of the hardness of the surface or the deformability of the surface.

15. The method of claim 1, wherein the at least one property of the surface is determined based on geo-location coordinates of the projected user interface.

16. The method of claim 15, wherein the geo-location coordinates of the projected user interface are determined using at least one of near field communication, Bluetooth, Geo fencing, indoor Wi-Fi positioning, or GPS.

17. The method of claim 15, wherein the user manually selects the relevant user interface setting for the surface and a current location of the user is tagged such that the selected relevant user interface setting are automatically selected to be the relevant user interface setting for user interfaces projected at the current location.

18. The method of claim 1, wherein the determined at least one property of the surface includes the deformability of the surface.

19. The method of claim 1, wherein the determined at least one property of the surface includes the hardness of the surface.

20. A method for adapting a property of a projected user interface based on at least one property of a surface on to which the projected user interface is projected, the method comprising:
determining the at least one property of the surface;
determining a relevant user interface setting based on the determined at least one property of the surface; and
applying the determined relevant user interface setting to the projected user interface, such that the property of the projected user interface is changed according to the determined user interface setting,
wherein the projected user interface is updated such that at least one of animations or sound effects of the projected user interface appear to match the at least one property of the surface, wherein:
on a less deformable surface, a pressed button results in a hard surface animation; and
on a more deformable surface, a pressed button results in a soft surface animation.

21. The method of claim 20, wherein at least one of:
the hard surface animation results in an element of the user interface bouncing higher than the soft surface animation; or
the hard surface animation is a hard scrolling animation that behaves differently than a soft scrolling animation by at least one of responding quicker, scrolling faster, or scrolling for a longer time.

22. A projecting device for projecting an interactive user interface onto a surface and for adapting a property of the projected user interface based on at least one property of the surface, the device comprising:
a projector configured to project the user interface onto the surface;
a sensor configured to determine the at least one property of the surface; and
a processor configured to:
determine a relevant user interface animation based on the determined at least one property of the surface, wherein the determined relevant user interface animation appears to match a physics of the surface; and
control the user interface projected by the projector such that the updating of the projected user interface in response to the user interaction with the elements of the projected user interface is applied according to the determined user interface animation based on the determined at least one property of the surface.

23. A system for projecting a user interface onto a surface and for adapting a property of the projected user interface based on at least one property of the surface, the system comprising:
the projecting device of claim 22; and
a computing device in communication with the projecting device.

24. The system of claim 23, wherein the computing device includes the projecting device.

* * * * *